United States Patent
Mauth et al.

(10) Patent No.: US 10,098,983 B2
(45) Date of Patent: Oct. 16, 2018

(54) BONE REPAIR MATERIAL

(71) Applicants: STRAUMANN HOLDING AG, Basel (CH); CAM BIOCERAMICS B.V., Leiden (NL)

(72) Inventors: Corinna Mauth, Basel (CH); Aaldert-Rens Molenberg, Basel (CH)

(73) Assignees: STRAUMANN HOLDING AG, Basel (CH); CAM BIOCERAMICS B.V., Leiden (NL)

( * ) Notice: Subject to any disclaimer, the term of this patent is extended or adjusted under 35 U.S.C. 154(b) by 0 days.

(21) Appl. No.: 15/476,012

(22) Filed: Mar. 31, 2017

(65) Prior Publication Data
US 2017/0203000 A1  Jul. 20, 2017

Related U.S. Application Data

(62) Division of application No. 14/374,101, filed as application No. PCT/CH2013/000027 on Feb. 12, 2013, now abandoned.

(30) Foreign Application Priority Data

Feb. 14, 2012 (EP) ..................... 12000934
May 2, 2012 (EP) ..................... 12003045

(51) Int. Cl.
*A61L 2/28* (2006.01)
*A61F 2/28* (2006.01)
(Continued)

(52) U.S. Cl.
CPC ............... *A61L 27/18* (2013.01); *A61L 27/10* (2013.01); *A61L 27/52* (2013.01); *A61L 27/54* (2013.01);
(Continued)

(58) Field of Classification Search
CPC ............... A61L 27/54; A61L 2300/414; A61L 27/3834; A61L 27/56; A61L 2430/02;
(Continued)

(56) References Cited

U.S. PATENT DOCUMENTS 6,511,510 B1  1/2003  de Bruijn et al.
7,012,034 B2  3/2006  Heide et al.
(Continued)

FOREIGN PATENT DOCUMENTS

EP  1 374 922 A1  1/2004
EP  1 457 214 A1  9/2004
(Continued)

OTHER PUBLICATIONS

Mar. 23, 2016 Office Action issued in U.S. Appl. No. 14/374,101.
(Continued)

*Primary Examiner* — Ann Schillinger
(74) *Attorney, Agent, or Firm* — Oliff PLC

(57) ABSTRACT

Sliceable bone repair material is a porous block-shaped scaffold containing a hydrogel, wherein the hydrogel is formed by Michael type addition of at least two precursor molecules. Said scaffold is made of a synthetic ceramic material and has interconnected macropores having a diameter above 100 μm. In addition said scaffold has a total porosity of 80 to 95%. The total volume of the hydrogel is smaller than the total volume of the interconnected macropores.

16 Claims, 3 Drawing Sheets

(51) Int. Cl.
| | |
|---|---|
| *A61L 27/18* | (2006.01) |
| *A61L 27/56* | (2006.01) |
| *A61L 27/10* | (2006.01) |
| *A61L 27/52* | (2006.01) |
| *A61L 27/54* | (2006.01) |
| *C08G 65/332* | (2006.01) |
| *C08G 65/334* | (2006.01) |
| *A61L 27/58* | (2006.01) |

(52) U.S. Cl.
CPC .............. *A61L 27/56* (2013.01); *A61L 27/58* (2013.01); *C08G 65/3322* (2013.01); *C08G 65/3342* (2013.01); *A61L 2300/414* (2013.01); *A61L 2430/02* (2013.01); *C08G 2210/00* (2013.01); *C08G 2230/00* (2013.01)

(58) Field of Classification Search
CPC .............. A61L 27/18; A61L 2300/412; A61L 2430/38; A61L 27/26; A61L 27/34; A61L 27/3608; A61L 27/3633; A61L 27/52; A61L 2400/06; A61F 2002/2817; A61F 2/28; A61F 2002/30583; A61F 2310/00179; A61F 2/30965; A61F 2/441; A61F 2002/2835; A61F 2310/00359; A61F 2/2846

See application file for complete search history.

(56) References Cited

U.S. PATENT DOCUMENTS

| | | |
|---|---|---|
| 2003/0143258 A1 | 7/2003 | Knaack et al. |
| 2004/0002770 A1 | 1/2004 | King et al. |
| 2005/0027367 A1 | 2/2005 | Heide et al. |
| 2005/0119762 A1 | 6/2005 | Zilla et al. |
| 2007/0059379 A1 | 3/2007 | Gerber |
| 2009/0043344 A1* | 2/2009 | Schlotterback ..... A61F 2/30756 606/86 R |
| 2011/0305745 A1 | 12/2011 | Gurtner et al. |

FOREIGN PATENT DOCUMENTS

| | | | |
|---|---|---|---|
| EP | 1 609 491 A1 | 12/2005 | |
| EP | 1 490 123 B1 | 9/2006 | |
| WO | 97/034546 A1 | 9/1997 | |
| WO | 03/040235 A1 | 5/2003 | |
| WO | WO 03040235 A1 * | 5/2003 | ............ A61L 27/18 |
| WO | 2004/011053 A1 | 2/2004 | |
| WO | 20040054633 A2 | 7/2004 | |
| WO | 2009/007034 A1 | 1/2009 | |
| WO | WO 2009007034 A1 * | 1/2009 | ............... A61F 2/28 |

OTHER PUBLICATIONS

Nov. 1, 2016 Office Action Issued in U.S. Appl. No. 14/374,101.
Aug. 27, 2015 Office Action issued in U.S. Appl. No. 14/374,101.
Mar. 20, 2013 International Search Report and Written Opinion in International Application No. PCT/CH2013/000027.
Mar. 20, 2013 International Search Report and Written Opinion in International Application No. PCT/CH2013/000028.
Jo, Yun Suk, et al., "Biomimetic Peg Hydrogels Crosslinked With Minimal Plasmin-Sensitive Tri-Amino Acid Peptides". Journal of Biomedical Materials Part A., 870-877, 2009, Wiley Periodicals, Inc.
Ghandehari, H., et al., "In Vitro Degradation of pH-Senstitive Hydrogels Containing Aromatic Azo Bonds". Biomaterials vol. 18, No. 12, 861-872, 1997, Elsevier Science Ltd., GB.
Almay, L. et al., "Biosynthetic Hydrogel Scaffolds Made From Fibrinogen and Polyethylene Glycol for 3D Cell Cultures". Biomaterials 26, 2467-2477, 2005, Elsevier Science Ltd., GB.

* cited by examiner

BONE REPAIR MATERIAL

This is a Division of application Ser. No. 14/374,101 filed Jul. 23, 2014, which in turn is a national stage of PCT/CH2013/000027, filed Feb. 12, 2013, which claims the benefit of priority of EP 12000934.5, filed Feb. 14, 2012, and EP 12003045.7, filed May 2, 2012. The disclosure of the prior applications is hereby incorporated by reference herein in its entirety.

FIELD OF THE INVENTION

The present invention relates to a sliceable bone repair material comprising a porous block-shaped scaffold containing a hydrogel. Said hydrogel is formed by Michael type addition of at least two precursor molecules. The scaffold is made of a synthetic ceramic material, comprises interconnected macropores and has a total porosity of 80 to 95%.

BACKGROUND

The repair of bone defects can be facilitated by placing a bone repair material as a temporary substitute in the defect site, where a loss of natural bone has occurred. The bone repair material is meant to selectively promote and guide the regeneration of natural bone structures.

Both naturally-derived and synthetically-produced bone repair materials have been used to repair such defects. Naturally-derived materials include grafts made from bones. The bone may be harvested directly from the patient, as in autograft-based procedures, or it may be harvested from a suitable donor, surrogate, or cadaver, as in allograft- or xenograft based procedures. However, autograft bone implant procedures are costly and cause additional discomfort for the patients, as they typically require an additional surgery for harvesting the graft material, which may cause significant morbity at the donor site. Autografts may also show pronounced resorption making the outcome of the augmentation unpredictable. Allogenic bone repair materials also unify osteoconductive and osteoinductive properties, but their origin raises possible pathogenic transfers and ethical issues. Similar concerns are brought up against xenogenic graft materials. Alternatively, naturally-derived bone repair materials may be replaced by a completely synthetic bone repair material, which contains no organic residues. In contrast to naturally-occurring bone repair materials, synthetic bone repair materials are often less osteoconductive and hardly osteoinductive. Nevertheless, much research has been and still is directed toward improved synthetic bone repair materials.

In oral surgery and orthopedics, synthetic bone repair materials on a hydroxyapatite (HA) and/or tricalcium phosphate (TCP) basis are widely used.

Depending on indications, they may be applied as granules or pre-fabricated blocks. U.S. Pat. No. 6,511,510 relates to a porous ceramic material from calcium phosphates obtained by a sintering process. The use of granular material allows treatment of a wide range of indications. For granular material, the ceramic block material is processed by steps such as rubbing, pounding and sieving afterwards (WO 04/054633). Although the granular materials are applied to a wide range of indications in terms of size and area, their suitability to treat large bone defects is limited, because they tend to migrate and as a result to be encapsulated. The augmented volume defined by the applied granules may collapse and fail to guide regrowth of the bone to its original dimensions. U.S. Pat. No. 7,012,034 describes a block-shaped bone augmentation material based on porous β-tricalcium phosphate.

Different approaches addressed the problem of providing a material with bone-like mechanical properties. In U.S. Pat. No. 6,994,726 a prosthetic bone implant is made of a hardened calcium phosphate cement having an apatitic phase as a major phase, which comprises a dense cortical portion bearing the majority of load, and a porous cancellous portion allowing a rapid blood/body fluid penetration and tissue ingrowth. Alternatively, EP 1 457 214 discloses a block shape organic-inorganic complex porous article with a superposed skin layer made of a degradable polymer with improved strength. The complex is mainly designed to be inserted between vertebral bodies.

To generally improve load bearing properties of bone repair materials, composite materials have been developed. EP 1 374 922 discloses a bioresorbable structure for use in the repair of bone defects comprising a porous bioceramic matrix of hydroxyapatite or tricalcium phosphate and a polymer disposed by compression molding therein. WO 97/34546 describes a ceramic block with a plurality of channels filled containing an enforcing bio-resorbant polymer material. In order to improve their regenerative potential, bone repair materials have been supplemented with bone growth inducing agents. U.S. Ser. No. 10/271,140 (US 2003/0143258A1) suggests a composite comprising demineralized bone matrix mixed with a stabilizing biodegradable polymer and a bone growth factor.

In a typical periodontal surgical bone repair procedure an incision is made in the gum tissue to expose a bone defect adjacent to a tooth root. Once the defect and root are debrided, a bone repair material, suspended in a suitable carrier is placed. The gum tissue is then closed, maintaining the repair material in place. Optionally, a barrier material may be utilized to retain the repair formulation in contact with the defect. Therefore, a bone repair material in periodontal surgery requires formulations that can be easily shaped to size and shape of the defect. WO 2004/011053 suggests a formulation with a putty consistency. Similarly, EP 1 490 123 describes a kneadable bone replacement material on a granular calcium phosphate and hydrogel basis. When applied to the defect site, the formulation remains adhered thereto without migration or excessive expansion. These concepts however, do provide for a solid bone substitute material.

US 2004/002770 discloses polymer-bioceramic structures for use in orthopaedic applications. Thereby a polymer is disposed in a porous bioceramic by compression molding.

WO 2009/007034 discloses a block-shaped scaffold and a hydrogel, wherein said scaffold comprises interconnected pores. Said interconnected pores are completely filled with a hydrogel. However, it has been found that the cells have difficulties to migrate into the scaffold material due to the presence of the hydrogel.

SUMMARY OF THE INVENTION

It was a problem of the present invention to provide a bone repair material which is easy to handle and suitable for treatment of large oral bone defects, which has osteoconductive and osteoinductive properties.

It was found that a sliceable bone repair material, wherein the total volume of the hydrogel that is evenly distributed within the scaffold is smaller than the total volume of the interconnected macropores shows excellent osteoconductive and osteoinductive properties.

The bone repair material according to the present invention comprises a porous block-shaped scaffold containing a hydrogel. Said hydrogel is formed by a Michael type addition of at least two precursor molecules. The scaffold is made of a synthetic ceramic material and comprises interconnected macropores having a diameter above 100 µm. In addition, the scaffold has a total porosity of 80 to 95%. Within the context of the present invention the term scaffold "containing" a hydrogel means that the hydrogel is evenly distributed within the macropores of the scaffold. Preferably, the outer surface of the scaffold is essentially free of hydrogel.

In a preferred embodiment said hydrogel is a reconstituted hydrogel. The term reconstituted hydrogel (also called rehydrated hydrogel) stands for a hydrogel obtained after rehydration of a dried hydrogel (xerogel).

The hydrogel comprised in the bone repair material according to the present invention has in its hydrated or reconstituted (rehydrated) form preferably a water content of more than 80% by weight, preferably more than 90% by weight, most preferably between 90 and 98% by weight. In a most preferred embodiment of the present invention the hydrogel with a PEG concentration of about 5% has a water content of 95% and a hydrogel with a PEG concentration of about 8% has a water content of about 92% by weight.

A dried hydrogel, also called xerogel, is the dry form of a hydrogel. Such a dry form of a hydrogel may be obtained by dehydrating a hydrogel under vacuum.

The equilibrium concentration is the ratio between the mass of the free precursor molecules and the mass of the swollen hydrogel at equilibrium. A swollen hydrogel at equilibrium is the cross-linked network of precursor molecules which is hydrated or reconstituted (rehydrated) with the amount of liquid it spontaneously takes up under physiological conditions (salt concentration, for example PBS buffer, and temperature, 37° C.). The water content of the hydrogel is dependent on the affinity of the polymer, that is PEG, and the density of the crosslinking points of the hydrogel. A swollen PEG hydrogel has preferably a water content of more than 90% by weight.

If the concentration of the precursor molecules in the bone repair material is clearly lower than the equilibrium concentration, that is 80% (90%), almost no crosslinking occurs. Due to the method which is disclosed below, it is possible to increase the concentration of the precursor molecules by water evaporating, and therefore, allowing the precursor molecules to crosslink. Best results were obtained for bone repair material, wherein the ratio of the total concentration of the precursor molecules and the equilibrium concentration of the total of the precursor molecules in the swollen hydrogel is less 0.9 to 0.95, since this bone repair material showed good osteoconductive properties and had no tendency to break.

Dependent on the porosity of the material, the PEG content (that is the total concentration of the at least two precursors) is adjusted in order to obtain good results.

In a preferred embodiment the ratio between the scaffold and total of the precursor molecules is greater than 18:1 by weight if the porosity is from 80 to 84%, greater than 13:1 by weight if the porosity is from 85 to 89%, greater than 8:1 by weight if the porosity is from 90 to 91%, and greater than 5:1 by weight if the porosity is from 92 to 95%.

Due to the ratio between the scaffold and the total of the precursor molecules in combination with the total porosity of the scaffold only 20 to 80%, preferably 30 to 60, most preferably 20 to 45% of the total volume of the interconnected macropores is filled with cross-linked hydrogel after rehydration, that is, the reconstituted hydrogel, which results in excellent osteoconductive and osteoinductive properties. Due to the fact that 40 to 70%, preferably 55 to 80% of the total volume of the interconnected macropores is empty, that means is filled with air, blood and tissue fluids, the cells can easily migrate into the scaffold material and therefore facilitate nutrient and oxygen supply, neo-vascularisation, cell immigration, colonization and bone deposition.

In a preferred embodiment the ratio between the scaffold and total of the precursor molecules is greater than 13:1 by weight, whereby the porosity of the scaffold is from 85 to 89%. Such a combination allows very good cell integration and an optimal bone repair material stability. Good results are also achieved for a bone repair material having a scaffold with a porosity from 90 to 91%, wherein the ratio between the scaffold and the total of the precursor molecules is greater than 8:1 by weight.

Due to the new method for preparing the bone repair material according to the present invention, which is described below in detail, the cross-linked hydrogel is distributed within the block-shaped scaffold. The inner surface of the pores is more than 50%, preferably more than 60% covered by a thin layer of the dried hydrogel, that is a xerogel, whereas interior space of the pore is not filled with hydrogel. After drying the hydrogel only 1 to 15%, preferably 2 to 15%, most preferably 2 to 5%, of the total volume of the interconnected macropores is filled with the dried cross-linked hydrogel. The expression "dried" hydrogel means, that it contains only small amounts of water, preferably less than 10%, most preferably less than 5%. The xerogel has a high porosity and an enormous surface area along with a small pore size. The so obtained bone repair material has due to the low water content an excellent shelf stability.

DETAILED DESCRIPTION

Figure 1:
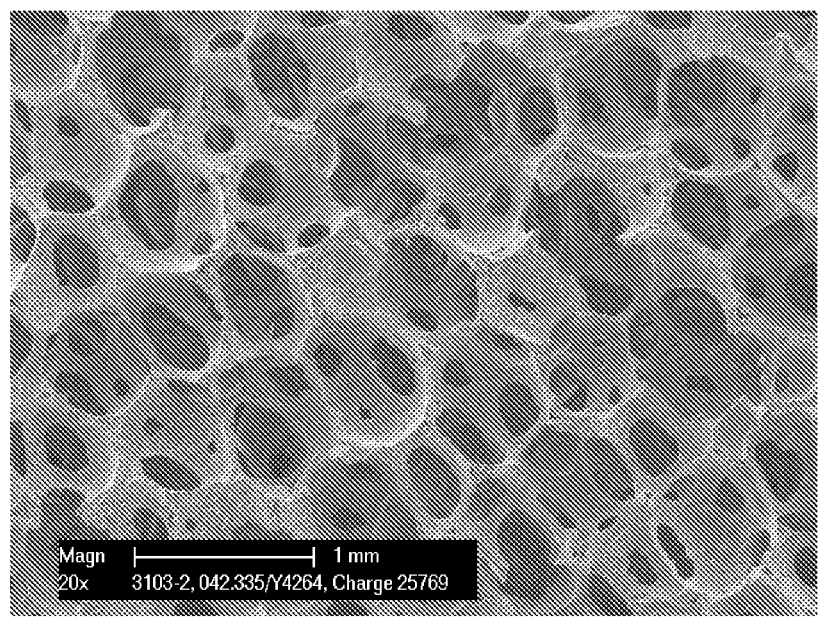
FIG. 1 shows an electron microscopy picture of a block-shaped scaffold which does not comprise a cross-linked polyethylene glycol hydrogel.
Figure 2:
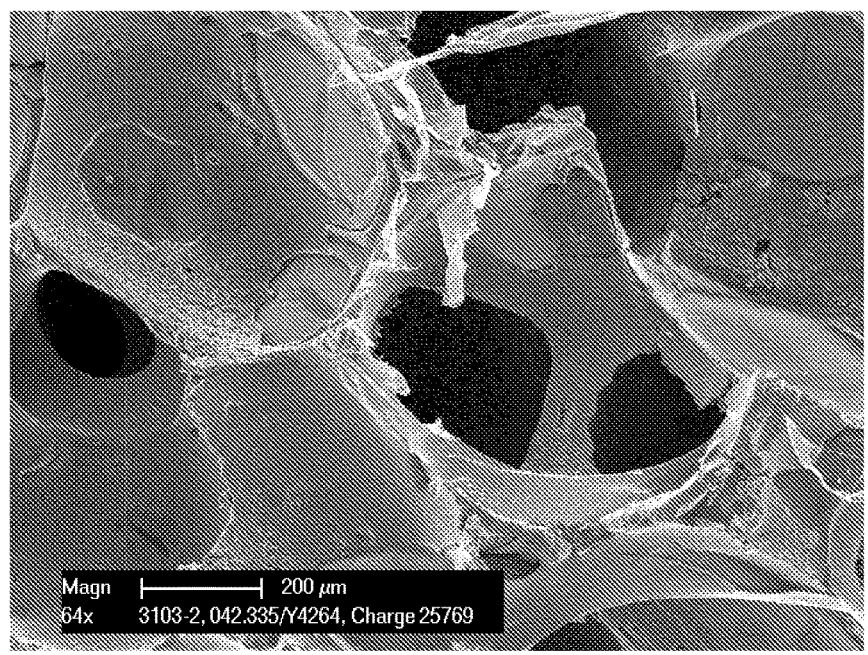
FIG. 2 shows an electron microscopy picture of a bone repair material according to the present invention containing a dried cross-linked polyethylene glycol hydrogel, that is a xerogel.

Beside the good osteoconductive properties the bone repair material according to the present invention has an excellent stability. In contrast thereto bone repair material having completely filled pores, has a tendency to break upon rehydration or swelling. Especially bone repair material, wherein only 20 to 30% of the total volume of the interconnected pores is filled with the hydrated or reconstituted cross-linked hydrogel, showed no tendency to break at all.

The scaffold of the bone repair material according to the present invention has interconnected pores and is made of a synthetic ceramic material. Preferably said synthetic ceramic material is a material comprising calcium phosphate. The synthetic ceramic material may be made of apatite, tricalcium phosphate or a mixture thereof. Apatite and tricalcium phosphate (TCP) or combinations thereof, are efficient bone substitutes that enhance bone ingrowth. Eventually, the material gets resorbed and substituted by bone.

Hydroxyapatite and β-tricalcium phosphate, and combinations thereof are especially preferred. These materials can be manufactured with well defined reproducible morphologies with respect to grain size and porosity.

The scaffold material according to the present invention has a porous morphology. Said scaffold material is a highly porous calcium phosphate with interconnected pores of a size range that allows fast ingrowth of natural bone. A person skilled in the art can determine the pore volume and the interconnectivity with micro CT. Methods to characterize calcium phosphate blocks with regard to the porosity have been described in Biomaterials, 2005 November; 26(31):6099-105 and in Biomaterials 27 (2006), 2776-2786.

For the preferred scaffold material according to this invention the total porosity lies in the range of 80 to 95%, preferably from 85 to 95%, most preferably from 85 to 90%. Porosity is the percentage of void space per volume unit of scaffold material. High porosity usually results in a large specific surface density, which is one important property increasing primary liquid absorption and protein adsorption throughout the whole material. Specific surface density is defined as the scaffold surface per scaffold volume. The preferred scaffold material according to this invention has a specific surface density of at least 20/mm, more preferably above 30/mm. The material will be integrated in newly formed bone and will eventually be degraded and replaced by natural bone. In the present invention the term porosity means only open pores, e.g. pores which are accessible from outside. Closed pores do not fall within said definition.

The expression the total volume of the interconnected macropores means the void space of all macropores. Typically, the void space of all macropores is measured by mercury intrusion porosimetry according to ISO 15901-1.

The porous structure may be obtained by various processes. Usually a powder is suspended in an aqueous solution to result in a slurry. To form a porous structure, a pore forming agent may be added. Alternatively a sponge-like polymeric matrix with a determined pore structure or an aggregate of spherical objects is coated with the slurry. After drying the slurry, the ceramic material undergoes a sintering process at high temperatures between 800° C. and 1300° C., depending on grain size and nanoporosity desired. During sintering the pore forming material is burned out and a porous ceramic scaffold remains. Depending on the process and the pore forming agent or material, the porosity of the block-shaped material can be adjusted to result in a desired distribution and interconnectivity of pores of various sizes. They can be classified as nanopores (diameter below 1 μm), micropores (diameter between 1 and 100 μm) and macropores (diameter above 100 μm). For the purpose of tissue regeneration, a substantial amount of interconnected micropores and macropores is desired in order to allow cells to migrate into the scaffold material. Preferably more than 90%, most preferably 95%, of the volume of the pores of the block-shaped scaffold are micropores and macropores. Micropores are mostly not connected to other micropores but to macropores. Their main function is to change the surface structure and area.

In a preferred embodiment of the invention, the diameter of the pores lies between 0.05 and 750 μm. More preferably, the diameter of the micropores is between 1 and 100 μm and the diameter of the macropores is between 100 and 1000 μm. Most preferably, the diameter of the micropores is between 5 and 100 μm and the diameter of the macropores is between 100 to 500 μm. The pores of the preferred scaffold material according to this invention have a mean diameter between 100 and 750 μm, preferably 300 and 600 μm. The preferred embodiment further has highly interconnected pores. The interconnectivity can be defined as connective density (equivalent to the terms connectivity or interconnectedness) as described in Bone, 1993 March-April; 14(2): 173-82. The scaffold material according to this invention has a connectivity, which is above 20 per mm$^3$. In terms of connections per pore, which is equal to the ratio of interconnectedness and the number of pores per volume, the scaffold material according to this invention has a connectivity per pore, which is at least 2, more preferably more than 3. As described above, the porosity does not need to be of random distribution, but may be obtained by a highly repeated spacing structure such as tubuli. A tubular structure with a suitable stabilizing polymer may be preferred, if high mechanical strength is required.

In addition to the composition and porosity, a suitable architecture of the block-shaped ceramic scaffold material may further enhance bone regeneration and improve the handling properties. A first portion of the block oriented to the remaining bone, which needs to be augmented, preferably has a cancellous structure with a high proportion of macropores, thereby facilitating the integration of bone tissue into the block. A second portion of the block-shaped ceramic scaffold material oriented to the surrounding soft tissue preferably has dense structure in order to reduce the risk of soft tissue ingrowth into the area of bone augmentation. Therefore, the ceramic scaffold material subject to this invention preferably is manufactured to contain a gradient in its porosity and/or crystallinity and/or ceramic composition.

As mentioned above the bone repair material according to the present invention comprises a cross-linked polyethylene glycol hydrogel. It could be shown that the porous block-shaped scaffold comprising a homogenously distributed cross-linked hydrogel has a waxy consistency, resulting in a bone repair material with excellent handling properties. The bone repair material is no longer brittle since the hydrogel stabilizes the pores, that is, it can be shaped with a scalpel, which is appreciated by the practitioner for fitting the block to the bone defect site.

The cross-linked polyethylene glycol hydrogels in this invention are based on the base catalyzed Michael type addition between a first precursor molecule and a second precursor molecule. In order to obtain a cross-linked network, at least one of the two precursors has more than two chains. The first precursor molecule has alpha, beta unsaturated carbonyl residues and the second precursor molecule has nucleophilic groups. The resulting linkage between the first precursor molecule and the second precursor molecule is an ester, which is unstable in contact with water. Alternatively, non-hydrolyzable linkages may be formed if maleimid or vinylsulfone groups are used. The PEG-thiol can be replaced by peptides with two cystein ends that are for example MMP sensitive to produce non-hydrolyzable but enzymatically degradable gels The rate of the hydrolysis reaction depends on the temperature on the chemical surrounding of the ester (for example acrylate vs methacrylate on precursor A, the number of methylene groups between O and S in precursor B) and the value of the pH, which is 7.4 in most tissues. When sufficient bonds have hydrolyzed, the cross-linked network degrades or breaks down. Therefore, the time of degradation of the network can be influenced by the number of hydrolysable bonds present per unit of volume. Such cross-linked polyethylene glycol hydrogels are described for example in EP 1 609 491.

The first precursor A preferably comprises a core which carries n chains with a conjugated unsaturated group or a conjugated unsaturated bond attached to any of the last 20 atoms of the chain. The later statement does not necessarily mean that the chains comprise at least 20 atoms; the chains may also be shorter, in which case the conjugated unsaturated group or a conjugated unsaturated bond is attached to an atom, which is closer to the end of the chain. In a preferred embodiment said conjugated unsaturated group or conjugated unsaturated bond is terminal. This means that said group is attached to the last atom of the chain, i.e. the one atom of the chain which is the furthest away from the core of the precursor molecule A. The core of the first precursor A can be a single atom such as a carbon or a nitrogen atom or a small molecule such as an ethylene oxide unit, an amino acid or a peptide, a sugar, a multifunctional alcohol, such as pentaerythritol, D-sorbitol, glycerol or oligoglycerol, such as hexaglycerol. The chains are polyethylene glycol chains. Beside the chains, the core of precursor A may be additionally substituted with linear or branched alkyl residues or polymers which have no conjugated unsaturated groups or bonds. In a preferred embodiment the first precursor A has 2 to 10 chains, preferably 2 to 8, more preferably 2 to 6, most preferably 2 to 4 chains.

The conjugated unsaturated bonds are preferably acrylate groups, acrylamide groups, quinine groups, 2- or 4-vinylpyridinium groups, vinylsulfone groups, maleimide groups or itaconate ester groups of formula Ia or Ib

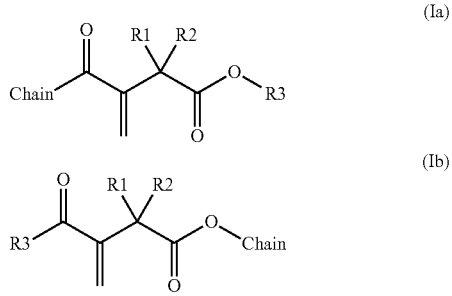

wherein R1 and R2 are independently hydrogen, methyl, ethyl, propyl or butyl, and R3 is a linear or branched C1 to C10 hydrocarbon chain, preferably methyl, ethyl, propyl or butyl.

In a most preferred embodiment the precursor A has a core which carries 2 to 6 polyethylene glycol chains, each chain having a terminal acrylate group (also called a multi-arm PEG acrylate). The core of the precursor A is preferably a pentaerythritol moiety.

The second precursor B comprises a core carrying m chains each having a thiol or an amine group attached to any of the last 20 atoms at the end of the chain. The later statement does not necessarily mean that the chains comprise at least 20 atoms; the chains may also be shorter, in which case the thiol or the amine group is attached to an atom, which is closer to the end of the chain. In a preferred embodiment said thiol or amine group is terminal or attached to the second to last carbon atom of the chain. The expression "terminal" means that said group is attached to the last atom of the chain, i.e. the one atom of the chain which is the furthest away from the core of the precursor molecule A. For example it would also be possible to incorporate a cysteine residue into the chain. Preferably the thiol group is terminal. The core of the second precursor B can be a single atom such as a carbon or a nitrogen atom or a small molecule such as an ethylene oxide unit, an amino acid or a peptide, a sugar, a multifunctional alcohol, such as pentaerythritol, D-sorbitol, glycerol or oligoglycerol, such as hexaglycerol. The chains are polyethylene glycol chains. In a preferred embodiment the second precursor B has 2 to 10 chains, preferably 2 to 8, more preferably 2 to 6, most preferably 2 to 4 chains.

In a most preferred embodiment the precursor B has a core which carries 2 to 4 polyethylene glycol chains, each chain having a terminal thiol group (also called a multi-arm PEG-thiol. The core of the precursor B is preferably an ethylene oxide group or a $CH_2$-group.

The first precursor A compound has n chains, whereby n is greater than or equal to 2, and the second precursor B compound has m chains, whereby m is greater than or equal to 2. The first precursor A and/or the second precursor B may comprise further chains which are not functionalized.

The sum of the functionalized chains of the first and the second precursor, that means m+n, is greater than or equal to 5. Preferably the sum of m+n is equal to or greater than 6 to obtain a well formed three-dimensional network. Such molecules having a core and two or more end groups are also referred to as multi-arm polymers.

Beside the number of chains, their length is a crucial parameter to adjust thy hydrolysis/degradation time of the hydrogel network and the mechanical properties of the bone repair material subject to this invention.

The number of atoms in the backbone (only carbon and oxygen atoms; hydrogen atoms are not counted) connecting two adjacent cross-linking points is at least about 20 atoms, preferably between 50 and 5000 atoms, more preferably between about 50 and 2000 atoms, most preferably between 60 and 1000 atoms, and ideally between 200 and 800 atoms. A cross-linking point is here defined as a point in which 3 or more backbone chains of the polymer network are connected.

In a preferred embodiment the first precursor has four polyethylene glycol chains having each an acrylate group as terminal group and a molecular weight of 15 kDa. The second precursor has four polyethylene glycol chains having each a thiol group as terminal group or attached to the second to last carbon atom of the chain and a molecular weight of 2 kDa. Such a hydrogel has an equilibrium concentration of about 8% by weight.

In a further preferred embodiment the first precursor has four polyethylene glycol chains having each an acrylate group as terminal group and a molecular weight of 15 kDa. The second precursor has two polyethylene glycol chains having each a thiol group as terminal group or attached to the second to last carbon atom of the chain and a molecular weight of 3.4 kDa. Such a hydrogel has an equilibrium concentration of about 5% by weight.

The precursors forming the cross-linked polyethylene glycol hydrogel are dissolved or suspended in aqueous solutions. Since no organic solvents are necessary, only aqueous solutions and/or suspensions are present. These are easy to handle and do not require any laborious precautions as might be the case if organic solvents were present. Furthermore, organic solvents are an additional risk for the health of the staff and the patients exposed to these solvents. The present invention eliminates said risk.

Said aqueous solution comprising the first and the second precursor can have a neutral pH or can be acidic, such as diluted acetic acid. To said solution or suspension optionally a bioactive agent may be added. Optionally said solution or suspension has to be diluted further in order to obtain a total polyethylene glycol concentration of less than 8, preferably less than 5% by weight (depending on the precursor used), in order to make sure that no gelation occurs. In a next step the pH of the suspension or solution is increased to a range of 7.0 to 9.5, preferably 8.0 to 9.5. Said suspension or solution is added to the scaffold. Then the bone repair material is dried under vacuum. Since water evaporates the concentration of the precursors increases and reaches the minimal gelation concentration and therefore gelation occurs. Typically, after drying under vacuum for 12 to 20 hours xerogel contained in the bone repair material according to the present invention has a water content of less than 10%, preferably of less than 5%. Before use said bone repair material, the xerogel has to be reconstituted by the surgeon, by rehydrating the dried hydrogel (xerogel) with water or with a buffered solution or soaking it for a few minutes in blood in order to allow the hydrogel to swell. Such a reconstituted swelled hydrogel comprises typically about 5% to 8% PEG in total and has a water content of 92 to 98% by weight.

In a preferred embodiment the cross-linked hydrogel comprised in the porous block-shaped scaffold has a pH in a range of 8.0 to 9.5, preferably from 8.6 to 9.5. The expression the hydrogel "has" a pH of for example 8.6 means that the hydrogel is formed at a pH of 8.6 or is after its formation brought to a pH of 8.6. That is, the pH is measured either a) in the buffered solution before adding said buffered solution to the precursors; or b) directly after mixing the precursor before crosslinking occurs; or c) in the buffered solution before adding the buffered solution to the dried product. Alternatively, the pH of the hydrogel can also be determined by calculation based on the projected amounts and concentrations of the reagents in the reaction mixture. Preferably the pH of the hydrogel is measured right after mixing the precursors, before soaking the scaffold with the mixture and before drying the bone repair material. Alternatively, the pH of the final product is adjusted by rehydrating the dried bone repair material in a buffered solution having the desired pH.

Surprisingly, it has been found that in the case of a bone repair material comprising a hydrogel having a pH in the rage of 8.0 to 9.5, preferably 8.6 to 9.5 the replacement of the hydrogel by newly formed bone is much faster than for hydrogels having a pH of about 7.6. Therefore, the bone regeneration takes place faster, leading to a shorter healing time. Although a difference of pH of about 0.5 to 1 may seem fairly small, it has to be noted that the pH is based on a logarithmic scale and that, therefore, a difference in pH of 1 corresponds to a difference in proton or hydroxide concentration by a factor 10.

The desired pH is achieved by addition of a basic catalyst or buffer regulating the pH. The concentration and the pH of the buffering agent may also be used to adjust the speed of gelation. For example, it may be used to increase the speed of gelation for not so dense gels. The final concentration in the mixture that is added to the bone repair material, e.g. triethanolamine, is preferably between 0.005 mol/l and 0.1 mol/l, preferably 0.01 mol/l.

In a further embodiment of the present invention the cross-linked polyethylene glycol hydrogel contained in the block-shaped scaffold is at the same time a matrix for sustained release of one or several bioactive agents, which promote the osteoconductive and/or osteoinductive properties of the composite bone repair material. As used herein, a bioactive agent is not limited by its origin or the way it is produced and therefore can be extracted, synthetically or recombinantly produced and may have been subject to further processing or purification, such as but not limited to, splicing, fragmentation, enzymatic cleavage or chemical modification. Examples of suitable biologically active agents are BMPs (e.g. BMP-2, BMP-7), PTH, VEGF, Enamel Matrix Derivatives (EMD) or proteins contained therein, TGF-beta, IGF, Dentonin, and cell recognition sequences such as RGD, KRSR, etc. Most preferred the bioactive agent is BMP or RGD.

The bioactive agent may be covalently bound to the hydrogel, e.g. this can be achieved by a thiol moiety present in the bioactive agent, which reacts with the conjugated unsaturated group or bond present in precursor A upon mixing. A thiol moiety is present, e.g., in the amino acid cystein. The bioactive agent is subsequently released from the hydrogel as the unstable ester linkage between the PEG and the bioactive agent is hydrolyzed.

Alternatively, the bioactive agents may simply be entrapped or precipitated into the bone repair material. The bioactive agent can be added when mixing the other components of the composition. The bioactive agent is then released by diffusion during and/or after degradation of the hydrogel. It is also possible to adsorb the bioactive agent on the block-shaped scaffold prior to the soaking with the solutions comprising the first precursor A and the second precursor B.

The mechanical strength of the block shaped scaffold can be further enhanced by embedding one or more additional stabilizing polymers, fibrous or filamentous supplements such as carboxy methyl cellulose, alginates, xanthan gum etc.

In a preferred embodiment the bone repair material is prepared as follows: In a first step a porous block-shaped synthetic scaffold is prepared comprising interconnected pores. Said scaffold has a total porosity of 80 to 95%.

In a second step an aqueous solution comprising the first precursor A is mixed with an aqueous solution of a second precursor B, whereby the concentration of the first precursor A and the second precursor B together is less than the equilibrium concentration of the swollen hydrogel, preferably less than 5% by weight, most preferably less than 4%, resulting in a mixture in which the total concentration of the reactive groups at the PEG molecules in the mixture is not high enough to allow the cross-linking reaction to reach the point of gelation, i.e. a gel does not form. Thus, depending on their molecular weights, the total concentration and the individual concentrations of the first precursor A and the second precursor B may differ.

In a third step the block-shaped synthetic scaffold is soaked in the mixture obtained in step two. Finally the bone repair material obtained in step three is vacuumed, resulting in a gradual increase of the concentration of the precursors, allowing the cross-linking reaction of the two precursors. The method is preferably carried out at room temperature. However, the temperature can be used to influence rate the rate of evaporation and of the crosslinking. Preferably, the bone repair material was dried slowly overnight under gradually increasing vacuum, in order to avoid foaming.

In a preferred embodiment the first precursor A has a concentration of 0.5% to 4.5% by weight, preferably of 1.5 to 4.5% by weight, most preferably 2.0 to 2.5% by weight, and the second precursor B has a concentration of 0.5% to 4.5% by weight, preferably of 0.5 to 3.0% by weight, most preferably 2.0 to 2.5%, before mixing them together, and the total concentration of the first precursor A and the second precursor B in solution added to synthetic ceramic scaffold is at least 2% by weight and less than 5% by weight, preferably less than 4% by weight.

Before use, the bone repair material has to be reconstituted by the surgeon by soaking the dried bone repair material in water, in aqueous saline solution, in a buffer solution or in blood. In the latter case the cells and factors are incorporated directly into the block. However, due to the fact that the pores of the block are not completely filled with the hydrogel, blood can also enter the bone repair material after soaking in water, aqueous saline solution, or a buffer solution.

In a preferred embodiment the surgeon is provided with a kit comprising repair material with the scaffold containing the xerogel (dried hydrogel) and a buffered solution, which is stored in a separate container or compartment. Before use, the surgeon soaks the bone repair material in the buffered solution in order to rehydrate the xerogel to reconstituted hydrogel in the bone repair material.

EXAMPLES

Example 1

Gelation Experiments Loose Hydrogels 6.4 mg of 4-arm PEG with acrylate end groups ($M_n$=15 kDa) and 3.3 mg of linear PEG with propylthiol endgroups ($M_n$=3.5 kDa) were dissolved in 64 µl of 0.04% aqueous acetic acid. To the solution 25 µl of 0.10 M triethanolamine were added, yielding a solution containing 9.8 wt % PEG. At 25° C. the solution yielded a soft, elastic hydrogel in 6.5 min.

3.3 mg of 4-arm PEG with acrylate end groups ($M_n$=15 kDa) and 1.7 mg of linear PEG with propylthiol end groups ($M_n$=3.5 kDa) were dissolved in 69 µl of 0.04% aqueous acetic acid. To the solution, 25 µl of 0.1 M triethanolamine were added, yielding a solution containing 5.0 wt % PEG. At 25° C. the solution yielded an elastic hydrogel, softer than the 9.8 wt % hydrogel in 16 min.

1.32 mg of 4-arm PEG with acrylate end groups ($M_n$=15 kda) and 0.69 mg of linear PEG with propylthiol end groups ($M_n$=3.5 kDa) were dissolved in 72.4 µl of 0.04% aqueous acetic acid. To the solution, 25 µl of 0.1 M triethanolamine were added, yielding a solution containing 2.0 wt % PEG. At 25° C. the solution did not yield a hydrogel within the observation time of 4 hours.

Example 2

Degradation Loose Hydrogels

A gel containing 9.8 wt % PEG was placed in PBS at pH 7.4 and 37° C. After 6 hours the gel had swollen to 2.2-fold its original weight. After that, swelling continued at a slower pace and after 11 days the gel was completely dissolved.

A gel containing 5.0 wt % PEG was placed in PBS at pH 7.4 and 37° C. After 6 hours the gel had swollen to 1.1-fold its original weight. After that, swelling continued at a slower pace and after 11 days the gel was completely dissolved.

Example 3

Gelation Experiment Denser Hydrogel 7.0 mg of 4-arm acrylate end groups ($M_n$=15 kDa) and 1.1 mg of 4-arm PEG with propylthiol end groups ($M_n$=2.3 kDa) were dissolved in 68.4 µl of 0.04% aqueous acetic acid. To the solution, 25 µl of 0.2 M triethanolamine/HCl buffer (pH 8.5) were added, yielding a solution containing 8.0 wt % PEG. At 25° C. the solution yielded a firm hydrogel in 2 to 3 min.

Degradation Denser Hydrogel

The denser gel containing 8.0 wt % PEG was placed in PBS at pH 7.4 and 37° C. After 6 hours the gel had swollen to 1.2 fold its original weight and after 28 days the gel was completely dissolved.

Example 4

Combination Bone Block and PEG Hydrogel
PEG a Solution:
356 mg of linear PEG with propylthiol end groups ($M_n$=3.5 kDa) were dissolved I 6.33 ml of 0.04% aqueous acetic acid.
PEG B Solution:
686 mg of 4 arm PEG with acrylate end groups ($M_n$=15 kDa) were dissolved in 6.00 ml of 0.04% aqueous acetic acid.
Activator Solution:
0.1 M triethanolamine in water.
5% PEG Hydrogel Hydrogel Solution
341 µl of PEG A solution, 341 µl of PEG B solution, 105 µl of water and 263 µl of activator solution were combined in a tube.
3% PEG Hydrogel Solution
204.8 µl of PEG A solution, 204.8 µl of PEG B solution, 483 µl of water and 157.5 µl of activator solution were combined in a tube.
2% PEG Hydrogel Solution
136.5 µl of PEG A solution, 136.5 µl of PEG B solution, 672 µl of water and 105 µl of activator solution were combined in a tube.
1% PEG Hydrogel Solution
68.3 µl of PEG A solution, 68.3 µl of PEG B solution, 861 µl of water and 52.5 µl of activator solution were combined in a tube.
Bone Block Immediately after mixing, the 1050 µl of hydrogel solution was applied to a bone block (8×8×20 mm3) with a porosity of 90% which absorbed the liquid completely.

The filled block was placed in an exsiccator that was heated to 37° C. and the pressure was gradually reduced to 5 mbar over the course of 5 hours, after which the block was left at 5 mbar and 25° C. for another 15 hours and finally, was kept at 37° C. again under high vacuum (<0.1 mbar) for 3 hours. This procedure almost completely removed the water without causing foaming and, in the process of water removal, allowed for efficient gelation.

It was observed that, upon prolonged incubation in cell medium (7 days at 37° C.) some blocks broke, presumably due to the pressure of the swelling hydrogel on the thin calcium phosphate wall of the bone block.

The ratio between scaffold (bone block) and total precursor molecules is also indicated.

| Scaffold [mg] | Precursor A [mg] | Precursor B [mg] | Total Precursor [mg] | Ratio scaffold/ total precursor | Wt % PEG in hydrogel | Blocks broken after 7 days |
|---|---|---|---|---|---|---|
| 404 | 19.2 | 39 | 58.2 | 6.9 | 5 | 50% |
| 404 | 11.5 | 23.4 | 34.9 | 11.5 | 3 | 8% |
| 404 | 7.6 | 15.6 | 23.2 | 17.1 | 2 | 0% |
| 404 | 3.85 | 7.8 | 11.65 | 34.7 | 1 | 0% |

Example 5

Minipig Implantation

An experiment with 36 adult female Göttingen minipigs has been carried out. 18 animals were sacrificed after 4 weeks and the remaining 18 animals after 12 weeks.

Bone blocks: Lot: SP081124B (dim.: 20×8×8 mm=1.28 cm$^3$, porosity 90%, 60 wt % hydroxyapatite and 40 wt % β-tricalcium phosphate.

The blocks were sterilized at 120° C. for 2 h and then oxygen plasma cleaned for 2.5 min at 35 W and 5 sccm gas flow. Total PEG concentration: 2% PEG (as described in Example 4), 1050 μl per block. Additionally rhBMP-2: Antigenix (cat. No. HC70034) has been added.

Figure 3:
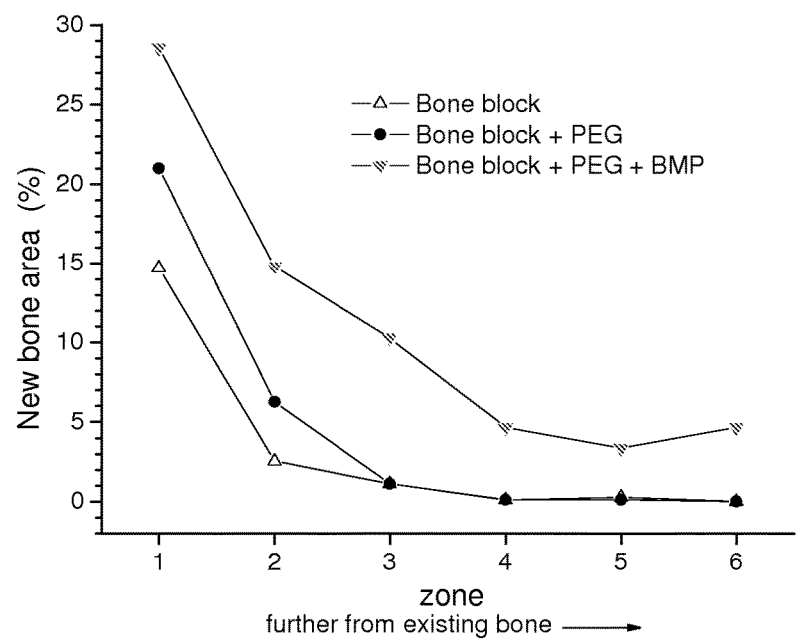
FIG. 3 is a graph of experimental results showing new bone area versus distance from existing bone according to one embodiment of the invention.

The results are shown in FIG. 3. It is clearly demonstrated that the bone block according to the present invention facilitates neo-vascularisation, cell immigration, colonization and therefore stimulates new bone growth.

What is claimed is:

1. A method for preparing a bone repair material, the method comprising:
    a. mixing an aqueous solution comprising a first precursor with an aqueous solution comprising a second precursor to form a mixture, a total concentration of the first precursor and the second precursor in the mixture being less than an equilibrium concentration of a hydrogel;
    b. adding the mixture to a porous block-shaped scaffold, the scaffold being made of a synthetic ceramic material and comprising interconnected macropores having a diameter of at least 100 μm, the scaffold having a total porosity in a range of from 80 to 95%; and
    c. removing water from the porous block-shaped scaffold containing the mixture to allow a Michael type addition reaction between the first precursor and the second precursor to produce a crosslinked polyethylene glycol hydrogel within the porous block-shaped scaffold.

2. The method according to claim 1, wherein the total concentration of the first precursor and the second precursor in the mixture is less than 5% by weight.

3. The method according to claim 2, wherein the first precursor is present in the mixture at a concentration in a range of from 0.5 to 4.5% by weight, and the total concentration of the first precursor and the second precursor in the mixture is at least 2% by weight.

4. The method according to claim 3, wherein the first precursor is present in the mixture at a concentration in a range of from 2.0 to 2.5% by weight.

5. The method according to claim 3, wherein the first precursor is present in the mixture at a concentration in a range of from 1.5 to 4.5% by weight.

6. The method according to claim 3, wherein the second precursor is present in the mixture at a concentration in a range of from 0.5 to 4.5% by weight, and the total concentration of the first precursor and the second precursor in the mixture is at least 2% by weight.

7. The method according to claim 6, wherein the second precursor is present in the mixture at a concentration in a range of from 0.5 to 3.0% by weight.

8. The method according to claim 6, wherein the second precursor is present in the mixture at a concentration in a range of from 2.0 to 2.5% by weight.

9. The method according to claim 2, wherein the second precursor is present in the mixture at a concentration in a range of from 0.5 to 4.5% by weight, and the total concentration of the first precursor and the second precursor in the mixture is at least 2% by weight.

10. The method according to claim 9, wherein the second precursor is present in the mixture at a concentration in a range of from 0.5 to 3.0% by weight.

11. The method according to claim 9, wherein the first precursor is present in the mixture at a concentration in a range of from 2.0 to 2.5% by weight.

12. The method according to claim 1, further comprising drying the hydrogel to a xerogel having a water content of less than 10% by weight.

13. The method according to claim 12, wherein water or a buffer solution is added to the bone repair material to reconstitute the xerogel.

14. The method according to claim 12, wherein the xerogel has a water content of less than 5% by weight.

15. The method according to claim 1, wherein the water is removed by vacuuming the porous block-shaped scaffold containing the mixture, and the vacuuming is increased over time.

16. The method according to claim 1, wherein the total concentration of the first precursor and the second precursor is less than 4% by weight.

* * * * *